United States Patent [19]

Aubin

[11] 4,344,435

[45] Aug. 17, 1982

[54] METHOD AND SURGICALLY IMPLANTABLE APPARATUS FOR PROVIDING FLUID COMMUNICATION WITH THE INTERIOR OF THE BODY

[76] Inventor: Norbert T. Aubin, P.O. Box 982, Loma Linda, Calif. 92324

[21] Appl. No.: 969,835

[22] Filed: Dec. 15, 1978

[51] Int. Cl.³ .................................... A61M 27/00
[52] U.S. Cl. ...................... 128/350 R; 3/1; 128/283
[58] Field of Search ............ 128/214 R, 349 BV, 283, 128/272, 350, 351, 278, 213, 1 R, 348; 3/1

[56] References Cited

U.S. PATENT DOCUMENTS

| | | | |
|---|---|---|---|
| 3,352,531 | 11/1967 | Kilmarx | 128/349 BV |
| 3,672,545 | 6/1972 | Marand | 128/278 |
| 3,752,162 | 8/1973 | Newash | 3/1 |
| 3,765,032 | 10/1973 | Palma | 3/1 |
| 3,783,868 | 1/1974 | Bokros | 128/348 |
| 3,815,577 | 6/1974 | Bucalo | 3/1 |
| 3,853,126 | 12/1974 | Shulte | 128/214 R |
| 3,923,065 | 12/1975 | Nozick et al. | 128/349 B |
| 4,092,983 | 6/1978 | Slivenko | 128/214 R |
| 4,187,850 | 2/1980 | Gust | 128/283 |

FOREIGN PATENT DOCUMENTS

| | | | |
|---|---|---|---|
| 472885 | 7/1969 | Switzerland | 128/1 R |
| 141591 | 7/1961 | U.S.S.R. | 128/350 R |
| 489510 | 2/1976 | U.S.S.R. | 128/213 |

*Primary Examiner*—Robert W. Michell
*Assistant Examiner*—T. J. Wallen

[57] ABSTRACT

The disclosure relates to a surgically implantable apparatus for providing selective fluid communication with the interior of the body of a patient. In a preferred embodiment, the apparatus includes an annular body permanently implanted in the abdominal wall and provides fluid communication to an internal tube placed in the gastrointestinal tract to facilitate feeding of a patient whose normal digestion process is inadequate. The internal tube is replaceable without surgery or removal of the annular body. The annular body houses a spring biased valve which is opened by coupling the annular body to an external conduit for nutrient fluid. The annular body includes flanges and tissue fixation material which permit regrowth of the abdominal wall tissue about the annular body.

13 Claims, 6 Drawing Figures

METHOD AND SURGICALLY IMPLANTABLE APPARATUS FOR PROVIDING FLUID COMMUNICATION WITH THE INTERIOR OF THE BODY

BACKGROUND OF THE INVENTION

The present invention relates to a surgically implantable apparatus for providing fluid communication with the interior of the body of a patient and, in specific embodiments, a permanently implanted, valved apparatus for introducing nutrient fluid into the gastrointestinal tract of the patient. Devices of this general type are classified as surgical cannula in class 128, subclass 348, of the United States Patent and Trademark Office files.

I. The Prior Art

The prior art gastrostomy tube (which Mr. Aubin used for a time prior to the implanting of an embodiment of the present invention) includes an internal tube which enters the gastrointestinal tract below the stomach through a surgical opening in the abdominal wall. The tube is made of semi-rigid plastic and is held in place by a balloon which is located in the gastrointestinal tract and inflated to retain the tube in place. A similar device is shown, for example, in U.S. Pat. No. 3,915,171 to Shermeta. The prior art gastrostomy tube exits the abdominal wall and may be held in place by taping it to the skin at the stomach. Normally the tube is closed by a cap. When the patient feeds himself he first removes the cap from the implanted tube, then removes the cap from a tube extending from a reservoir of nutrient fluid such as a kangaroo bag and, finally, couples the two tubes together. The nutrient fluid passes from the reservoir into the intestinal system.

This system has a number of disadvantages, the most serious of which is that the gastrostomy tube tends to move around and irritate the opening in the abdominal wall and the diseased intestinal tract. The irritation may lead to infection which, in some cases, may be fatal. In fact, the opening in the abdominal wall can become very irritated by even slight movement of the plastic tubing. The raw flesh at the opening and projecting tube is very unsightly. In addition, perhaps because of a pressure change or muscular contraction, the tube may move downward through the intestinal tract. In such a situation the tube might be drawn into the intestinal tract through the opening in the abdominal wall. The tube can also be accidentally pulled, for example, during feeding when the patient is coupled to a fluid reservoir. Such movement is extraordinarily painful to the patient.

Additional difficulty with the prior art device arises from the fact that the gastrostomy tube itself deteriorates at a variable rate and may require surgery for replacement at intervals of, for example, 6 months or a year.

Finally, the gastrostomy tube is difficult to manipulate and uncap to prevent the contents of the stomach or the contents of the reservoir from being spilled during the coupling and feeding operation.

Patients who have the prior art gastrostomy implanted, such as Mr. Aubin, frequently decline as a result of the pain and surgery. This coupled with the difficulties in feeding and the unsightly appearance of the tube and raw opening can take away a patient's will to live.

Other surgically implantable cannula known in the prior art include the device described in U.S. Pat. No. 3,540,451 to Zeman. Specifically, Zeman discloses a cannula implanted in the body which includes tubing connecting a first flanged annular body placed in an opening of the abdominal wall with a second flanged annular body placed in an opening in a hollow organ. The tube is opened by removing a threaded sealing pin carried by an opening of the device external of the body. Whether the Zeman device has ever been successfully used for a gastrostomy or similar function or whether permanent fixation to abdominal tissue has been achieved is unclear. However, the device has numerous apparent disadvantages including, inter alia, that replacement of the internal tube would require surgery, and that connection to an external conduit requires removal of the sealing pin.

Of more general interest are Swiss Pat. No. 472,885 to Potrueil and the following U.S. Patents.

| Pat. No. | Inventor | Issue Date |
| --- | --- | --- |
| 1,383,209 | Iftiger | June 28, 1921 |
| 3,241,554 | Coanda | March 22, 1966 |
| 3,570,484 | Steer et al | March 16, 1971 |
| 3,752,162 | Newash | August 14, 1973 |
| 3,783,868 | Bokros | January 8, 1974 |
| 3,893,446 | Miller | July 8, 1975 |
| 3,998,222 | Shihata | December 21, 1976 |
| 4,092,983 | Slivenko | June 6, 1978 |

II. Objects of the Invention

Accordingly, it is an object of the present invention to provide a permanently implantable device for providing fluid communication with an internal organ of the patient.

It is another object of the present invention to provide a device which is permanently implanted in the abdominal wall of the body to provide fluid communication to a tube located in the gastrointestinal tract of the patient.

It is another object of the present invention to provide a device which is permanently surgically implanted in the abdominal wall to provide fluid communication to a tube located in the gastrointestinal tract of the patient, which tube can be inserted or removed and replaced without further surgery.

It is another object of the present invention to provide a surgically implanted device for providing selective communication with an internal organ of the patient responsive to the coupling of the device with an extracorporeal conduit.

It is another object of the present invention to provide a valved device for surgical implantation in the abdominal wall of a patient, which device can be disassembled for repair or cleaning without further surgery.

It is another object of the present invention to provide an implant for the abdominal wall for establishing fluid communication with an internal organ, which implant is adjustable to accommodate variations in the thickness of the abdominal wall.

It is another object to provide a device for use in a gastrostomy, which device is fixed to the abdominal wall by tissue regrowth and is nearly flush with the skin of the abdominal wall.

These and other objects and features of the invention will become apparent from the claims and from the

THE DRAWINGS

DETAILED DESCRIPTION

Figure 1:
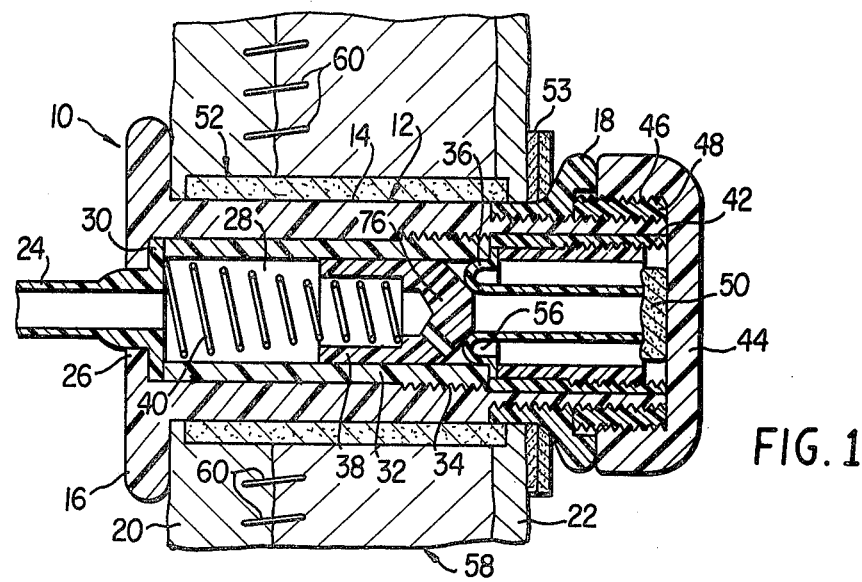
FIG. 1 is a cross-sectional view of a surgical implant of a preferred embodiment of the present invention.

The present invention relates to an apparatus for providing selective fluid communication with the interior of the body through a surgical opening in the body. While reference is generally made herein to the use of the apparatus in the body of a "patient". It will be understood that the claimed devices may have veterinary or scientific application in living animals as well as in human patients. Such applications are included within the meaning of the terms "body" and "patient", when used in describing the use environment of the apparatus.

In a preferred embodiment of the present invention the apparatus may be employed for providing fluid communication with the gastrointestinal tract of a patient through an opening in the abdominal wall and gastrointestinal tract. More particularly, the apparatus may be used in a gastrostomy, ileostomy, colostomy, etc. In such applications the apparatus is used to facilitate the supply and/or removal of fluid from the stomach or intestines when, for some reason, the gastrointestinal tract cannot be supplied or relieved in the normal way. For example, the apparatus may be used in a gastrostomy to feed a patient suffering from a disease of the digestive tract such as regional illeitus. In this example the apparatus is used to supply fluids to the gastrointestinal tract. However, the apparatus may be used in a colostomy for removing feces from the colon when the elimination function cannot be performed naturally. Moreover, the apparatus can be employed for administering non-caloric fluids for weight control. As a final example, the disclosed apparatus can be used as an ileal conduit for a ureterostomy to relieve the kidneys when, through disease, the ureters or bladder are not able to perform this function.

A preferred embodiment of the present invention includes a spool-shaped member for insertion through openings in the abdominal wall and gastrointestinal tract, the spool-shaped member having an axial bore therein. The spool-shaped member may consist of an annular body with a first, radially outwardly extending concentric flange for location at an interior side of a gastrointestinal tract wall and a second radially outwardly extending concentric flange at another end thereof, threaded on the annular body, for tightening against the external surface of the abdominal wall to inhibit movement of the annular body into the patient and to permit adjustment of the apparatus for variations in the thickness of the abdominal wall.

The annular body may also include a concentric radially inwardly extending flange which narrows the bore of the annular body. A flexible cannula may be provided for insertion into the gastrointestinal tract, the cannula having a radially outwardly extending flange for engaging the inwardly extending flange of the annular body to retain the cannula in place. The spool-shaped member may have attached thereto on an outer circumference, a sleeve of dacron felt for facilitating fixation of the tissue of the abdominal wall to the spool-shaped member.

A valve may be carried within the annular body, the valve being normally biased to block fluid flow through the bore of the annular body. A coupling may be provided for a conduit external to the patient, the coupling having a pin or similar means for opening the valve when the coupling is coupled to the spool-shaped member. Alternatively, the valve may be opened by fluid pressure from a pump supplying fluid to the gastrointestinal tract.

Telescoping threaded sleeves may be provided in the annular body to permit selective removal of the flexible cannula or the valve mechanism for cleaning or replacement, without requiring further surgery.

With reference to the drawings, a surgical implant of a perferred embodiment of the present invention is denoted generally by the numeral 10 in FIGS. 1-5. The apparatus may consist of a spool-shaped member 12, having a central cylindrical portion 14, a first flange 16 at one end thereof and a second flange 18 at the other end thereof. The first flange 16 is a radially outwardly extending concentric flange for location at the interior side of the wall 20 of the gastrointestinal tract to inhibit movement of the annular body out of the patient. The second flange 18 may comprise a threaded member concentric with the central cylindrical portion 14 for tightening against an external surface 22 of the abdominal wall of the patient to inhibit movement of the spool-shaped member into the patient and to permit adjustment of the apparatus for variations in thickness of the abdominal wall.

The apparatus may include a flexible cannula 24, inserted in the bore of the spool-shaped member for providing fluid communication between the gastrointestinal tract and the exterior of the body. The flexible cannula 24 may be held in position by means of a radially inwardly extending flange 26 of the spool-shaped member which narrows the bore 28 of the spool-shaped member and engages a corresponding flange 30 of the cannula 24. Advantageously, the flexible cannula may comprise a section of plastic tubing, opened at both ends or having a perforated section at a selected position in the gastrointestinal tract.

In the bore 28 of the spool-shaped member, a first threaded sleeve 32 may be provided for engaging corresponding threads 34 in the spool-shaped member and for selectively securing the flange 30 of the cannula in sealing engagement with the spool-shaped body. The first threaded sleeve may be removed to selectively release the flange of the cannula to permit the cannula to be withdrawn from the bore of the spool-shaped body. This feature of the embodiment will be described in greater detail in connection with FIG. 4 below.

A valve mechanism may be carried within the bore 28 of the spool-shaped member. The valve mechanism may include a valve seat 36, a valve body 38, axially moveable in the bore of the spool-shaped member, and a spring 40 for biasing the valve body 38 against the valve seat 36. A second threaded sleeve 42 may be provided for selectively securing the valve seat 36 in position and, alternately, selectively releasing the valve seat to permit removal of the valve set from the annular body. The operation of the valve mechanism is described in connection with FIG. 4, below.

A threaded cap 44 may be provided for engaging corresponding threads 46 on the spool-shaped body to close access to the valve and bore of the apparatus. Advantageously, the threads 46 may be provided on a double threaded spacer 48 located between the threaded cap 44 and a cylindrical portion of the spool-shaped member 12. A pad 50, impregnated with a deodorant, may be located in the bore of the annular body and held in position by the cap 44 to reduce the effect of undesirable odors eminating from the apparatus.

Figure 1A:
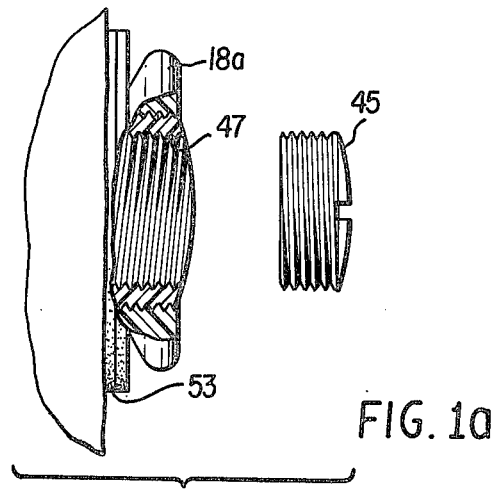
FIG. 1a is a cross-sectional view of a portion of the surgical implant of FIG. 1 showing an alternate configuration of the cap structure.

An alternate embodiment of the cap structure is shown in FIG. 1a. In the alternate embodiment a threaded cap 45 is provided with circumferential threads for engaging threads 47 of the spool-shaped member. This arrangement has the advantage that apparatus may be located nearly flush with the skin of the abdomen.

The spool-shaped member 12 may be made from a physiologically innert substance such as carbon 99 or polytetrafluoroethylene (TEFLON). When the apparatus is fabricated from fluorinated hydrocarbons the apparatus may be coated with from 1 to 4 thousanth of an inch of cured silicone.

The apparatus is intended to be used in a permanent or semi-permanent application wherein abdominal tissue regrowth holds the implant in place in the abdominal wall. For this purpose, a cylindrical sleeve 52 of dacron felt may be glued to the cylindrical portion 14 of the spool-shaped member 12. Advantageously, the gluing may be accomplished with a cement such as the cement identified as General Electric #18. Tissue fixation may be achieved by soaking the dacron felt in the blood of the patient and sewing the flesh to the dacron felt. Flexible plastic foam washers 53 may be provided between the patient's skin and the second flange 18 to prevent the dacron felt from touching and irritating the skin. It also may prevent any acid from the body from leaking until the incision is healed.

The following procedure may be employed to surgically implant the apparatus described in connection with FIG. 1. The patient is placed under a general endotracheal anesthetic. After this is done the patient's abdomen may be entered through an abdominal incision. In the case that the apparatus is to be used in a gastrostomy, the stomach may be entered through an incision therein. The implant described in FIG. 1 may then be taken from a sterilizing autoclave and placed into the stomach. The apparatus may be secured in place with two pursestring sutures, the innermost one being placed with 00 general closure Dexon, the outermost layer being placed with 0 general closure Dexon. The apparatus may then be brought through the anterior abdominal wall through the incision made earlier. The second, exterior flange 18 may then be secured in place. With the use of interrupted 00 silk stitches 60, the stomach may be affixed to the anterior abdominal wall 58. The operation may be terminated by closure of the abdomen using the Tom Jones closure technique and #1 general closure Dexon. The skin may be closed with the use of a running continuous subcuticular Dexon of 000. No retention sutures need be used.

In order that the apparatus be dimensioned correctly to provide proper separation between the flanges 10 and 18, a sonar measurement may be made prior to surgery to determine the thickness of the abdominal wall. The sonar measurement is performed in the conventional manner.

It should be understood that the apparatus of FIG. 1 may be surgically implanted either with or without the flexible cannula 24. Once the spool-shaped member is in place in the patient, the flexible cannula may be inserted either during or after surgery.

Figure 2:
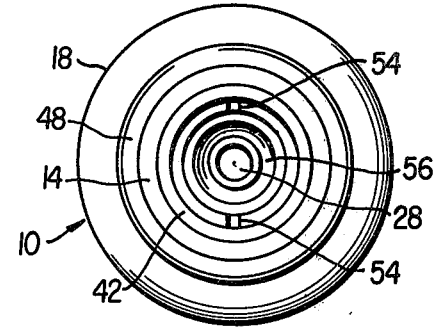
FIG. 2 is a pictorial view of an exposed end of the implant of FIG. 1 with the protective cap removed.

FIG. 2 is a pictorial view of an externally facing end of the implant shown and described connection with FIG. 1, with the cap 44 removed. Like structures and features are identified by the said numerals as used in FIG. 1.

As shown in FIG. 2, the sleeve 42 is concentric with the bore 28 of the spool-shaped member and the external, adjustable flange 18. Notches 54 may be formed in the sleeve 42 for engaging a tool to permit the unscrewing of the flange and removal thereof.

As shown best in FIG. 2 the valve seat 36 may be annular in shape having a concentric indentation 56 for receiving the coupling of an extracorporeal conduit.

Figure 3:
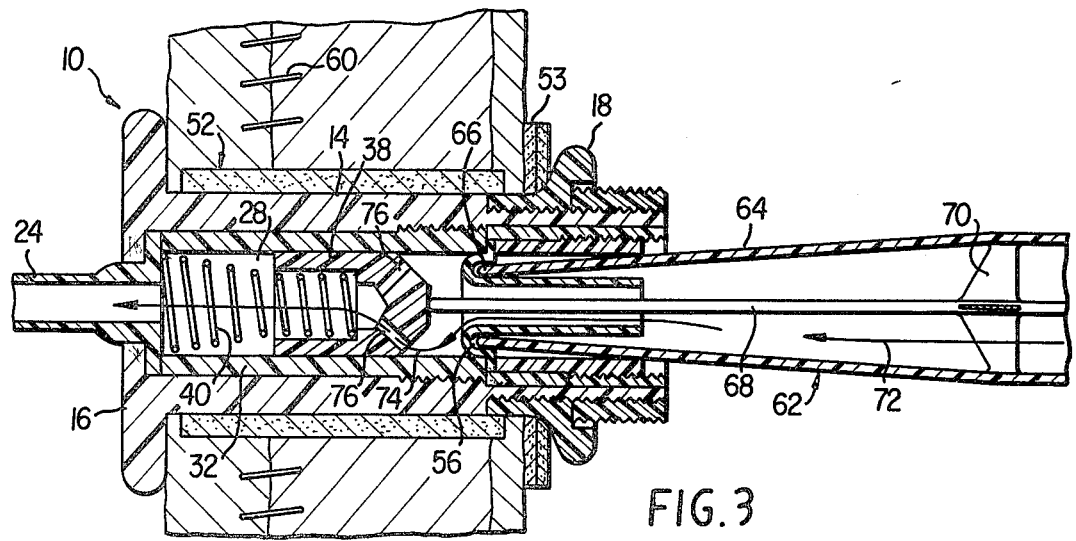
FIG. 3 is a cross-sectional view of the implant of FIG. 1, with a coupling inserted therein.

The use of the apparatus of FIG. 1 for feeding a patient is described now in connection with FIG. 3, wherein like numerals are used to identify like structures and features shown in FIG. 1. In FIG. 3 the apparatus is shown in use as a gastrostomy. The apparatus is depicted with the cap 44 removed to permit introduction of fluid into the gastrointestinal tract via the apparatus.

When the patient is to be feed, the cap 44 is removed and a coupling 62 may be inserted in the exposed orifice of the apparatus. Advantageously, the coupling 62 may consist of a rigid or semi-rigid, hollow, truncated cone-shaped sleeve 64, which communicates with an extracorporeal conduit through which nutrient fluid is supplied. An end portion 66 of the sleeve 64 may be dimensioned and configured to couple with the annular indentation 56 in the valve seat 36. The coupling 62 may also be provided with a pin 68 held in position along the longitudinal axis of the sleeve 64 by radially extending vanes 70. It will be understood that fluid may past through the coupling 60 to between the vanes 70 as indicated by the double-headed arrow 72.

The pin 68 of the coupling 62 is provided to actuate the valve mechanism carried in the bore 28 of the apparatus. It will be clear from the examination of FIG. 3 that the insertion of the coupling 62 into the orifice of the apparatus will cause the pin 68 to contact the valve body 38. Pressure exerted on the coupling 62 against the bias exerted by the spring 40 will cause the valve body 38 to move away from the valve seat 36. This axial movement of the valve body 38 permits fluid to flow along the path indicated by the double-headed arrow 74, i.e., through the sleeve 64, through the valve seat, through apertures 76 in the valve body 38, through the bore as defined by the threaded sleeve 32, and, finally, into the flexible cannula 24.

It will be readily understood that the apparatus described may be used for removing fluids from the gastrointestinal tract, as opposed to introducing fluids into the tract as described above. In such a situation the directions of flow indicated by the arrows 72 and 74 would be reversed. In addition the valve may be opened by fluid pressure rather than by the coupling. If the valve is reversed biased, the valve may be opened by a vacuum pump to permit withdrawal of fluids from the gastrointestinal tract.

Figure 4:
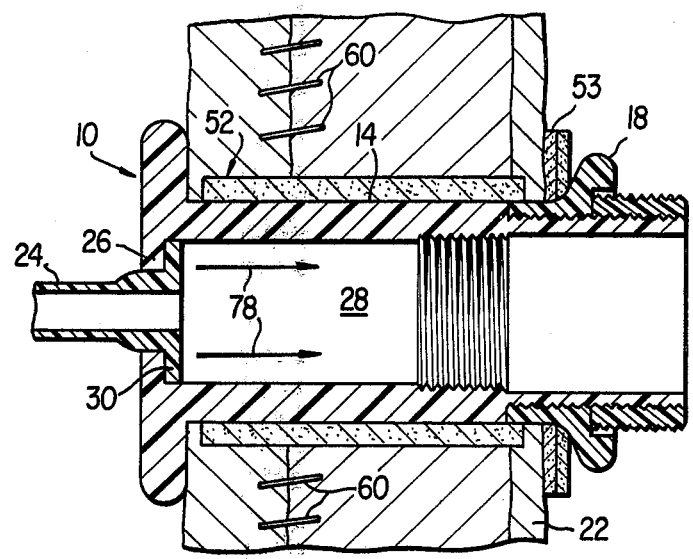
FIG. 4 is a cross-sectional view of the implant of FIG. 1 with the valve and coupling mechanism removed.

FIG. 4 illustrates the insertion or removal of the flexible cannula 24. In FIG. 4 like structures and features discussed in connection with FIGS. 1–3 are identified with the same numerals. In FIG. 4, the apparatus of a preferred embodiment of the present invention is shown with the sleeve 32 removed. It will be recalled that the sleeve 32, when in position as shown in FIG. 1, functions to maintain the flange 30 of the flexible cannula 24 in sealing engagement with the flange or narrowed region 26 of the spool-shaped body 14.

Should, for example, the flexible cannula require replacement due to deterioration over time in the gastrointestinal tract of the patient, the sleeve 32 could be removed to permit withdrawal and replacement of the flexible cannula 24. In such a situation a pair of forceps may be employed to grasp an end of the cannula 24 and withdraw the cannula through the bore 28 in the direction indicated by the arrows 78. Then, a replacement cannula can be inserted through the bore 28 and seated on the flange or narrowed portion 26 of the spool-shaped body 14. Once this has been accomplished, the sleeve 32 and valve mechanism can be reinserted in the apparatus to seal the flange 30 against the flange 26 and to permit normal operation of the apparatus to be resumed.

Figure 5:
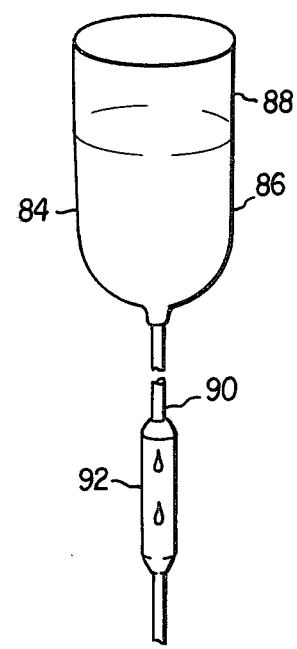
FIG. 5 is a pictorial view in partial cross-section of a stomach, gastrostomy and nutrient fluid supply, employing a embodiment of the present invention.
Figure 5:
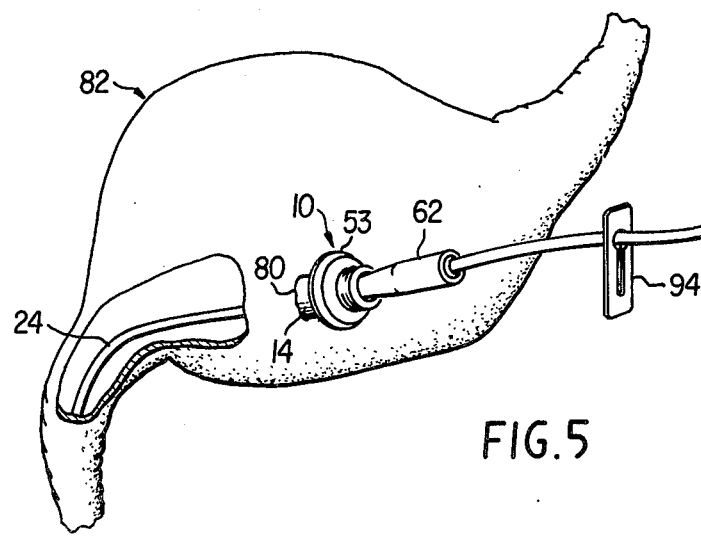

FIG. 5 shows the apparatus 10 of a preferred embodiment of the present invention in use as a gastrostomy for feeding a patient nutrient fluid. For clarity sake, the abdominal wall of the patient has been eliminated. As shown in the figure the spool-shaped member 14 of the apparatus is placed in an opening 80 in the wall of the patient stomach 82. The stomach is drawn in partial cutaway to show the location of the flexible cannula 24 in the gastrointestinal tract.

Nutrient fluid 84, for example a partially digested food such as Isocal, is provided in a reservoir 86 (the hanging kangaroo bag 88). When the patient is to be fed, the cap 44 (not shown in FIG. 5) is removed from the apparatus and the coupling 62 is inserted therein. As described in connection with FIG. 3, the insertion of the coupling opens the valve mechanism to permit fluid flow into the gastrointestinal tract. The nutrient fluid 84 from the reservoir 86 may flow to the coupling 62 via an extracorporeal conduit 90. The conduit 90 may be provided with a conventional drip meter 92 for monitoring the rate of flow of the nutrient fluid. The conduit 90 may also be provided with a pinch valve 94 for selectively interrupting flow of fluid through the conduit.

It will be readily understood that by employing the apparatus of the present invention the patient may feed himself through the gastrostomy in a simple clean and efficient manner which avoids the possibility of movement of the cannula and apparatus in the patient's gut and, therefore, avoids the possibility of pain and injury to the patient associated with unwanted movement of the apparatus. In addition, the internal cannula employed in the apparatus may be replaced without pain or surgery to the patient. Finally, the feeding apparatus including the coupling and reservoir may be connected to the gastrostomy with little or no spillage of the nutrient fluid or the contents of the gastrointestinal tract.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. A surgically implantable apparatus for a gastronomy, comprising:
    a hollow, generally cylindrical elongated body for insertion through a surgical opening in the abdominal wall and stomach wall of the patient, said cylindrical body having
    a radially outwardly extending concentric flange for location at the interior side of the stomach wall to inhibit movement of the cylindrical body out of the patient; and
    a concentric radially inwardly extending flange which narrows the bore of the cylindrical body;
    means, attached around the circumferential surface of the cylindrical body, for facilitating fixation of the tissue of the abdominal wall to the cylindrical body;
    a flange member, threaded concentrically on the cylindrical body for tightening against the external surface of the abdominal wall to inhibit movement of the cylindrical body into the patient and to permit adjustment of the apparatus for variations in thickness of the abdominal wall;
    a flexible cannula for insertion in the gastrointestinal tract of the patient, said cannula having radially outwardly extending flange for engaging the inwardly extending flange of the cylindrical body;
    a first threaded sleeve for engaging corresponding threads in the bore of the cylindrical body and for selectively securing the flange of the cannula in sealing engagement with the cylindrical body and alternatively, selectively releasing the flange of the cannula to permit the cannula to be withdrawn through the bore of the cylindrical body;
    a valve seat;
    a second threaded sleeve concentric with the cylindrical body for selectively securing the valve seat in position and alternatively, selectively releasing the valve seat from the cylindrical body; and
    a valve body, moveable along the axis of the cylindrical body away from the valve seat responsive to the insertion into the apparatus of the couping of a extracorporeal conduit.

2. The apparatus of claim 1 further comprising a spring means for normally biasing the valve body against the valve seat.

3. The apparatus of claim 2 wherein removal of the second threaded sleeve permits removal of the valve seat, valve body and spring means for cleaning.

4. The apparatus of claim 1 further comprising a threaded cap for engaging corresponding threads on the cylindrical body to close access to the bore of the cylindrical body.

5. The apparatus of claim 4 further comprising a pad impregnated with a deodorant located in the bore of the cylindrical body.

6. The apparatus of claim 1 wherein the valve seat is annular in shape having a concentric indentation for receiving the coupling of the extracorporeal conduit.

7. The apparatus of claim 1 wherein the cylindrical body is physiologically inert and is formed from polytetrafluoroethylene, coated with one to four thousandths of an inch of cured silicone.

8. The apparatus of claim 7 wherein the tissue fixation means includes a cylindrical sleeve of dacron foam glued to the cylindrical body.

9. The apparatus of claim 8 further comprising a flexible foam washer, concentric with the cylindrical body, for insertion between the external surface of the abdominal wall and the flange member for tightening against the external surface of the abdominal wall.

10. An apparatus for providing fluid communication with the gastrointestinal tract of a patient through openings in the abdominal wall and gastrointestinal tract of the patient, comprising:
- a spool-shaped member for insertion through the openings in the abdominal wall and the gastrointestinal tract, said spool-shaped member having an axial bore, narrowed in a portion thereof;
- means attached to an outer surface of the spool-shaped member for facilitating fixation of the tissue of the abdominal wall to the spool-shaped member;
- a flexible cannula for extending into the gastrointestinal tract, said cannula having a flanged portion; and
- means for selectively securing the flanged portion of the cannula in sealing engagement with the spool-shaped member and alternately, selectively releasing the cannula to permit the cannula to be withdrawn through the bore of the spool-shaped member whereby the flexible cannula can be replaced without surgery.

11. An apparatus for providing selective fluid communication with the gastrointestinal tract of a patient through an opening in the abdominal wall of the patient comprising:
- an annular body for insertion and fixation to the abdominal wall having a bore communicating with the gastrointestinal tract;
- a valve carried within the annular body, normally biased to block fluid flow through the bore of the annular body, wherein the valve carried within the annular body includes a valve body spring biased outwardly with respect to the patient against a valve seat; and
- a coupling for a conduit external to the patient, the coupling having means for opening the valve when the coupling is coupled to the annular body wherein the coupling comprises a sleeve dimensioned to permit insertion in the bore of the annular body and wherein the means for opening the valve is an elongated member located on the axis of the sleeve and adapted to move the valve body inwardly with respect to the patient against the spring bias to open the valve.

12. The apparatus of claim 11 wherein the external conduit is connected to a reservoir of nutrient fluid which is elevated to cause flow of the nutrient fluid into the gastrointestinal tract of the patient.

13. A surgically implantable apparatus for providing fluid communication with the gastrointestinal tract of a patient comprising:
- a hollow, generally cylindrical elongated body for insertion through a surgical opening in the abdominal wall and the wall of the gastrointestinal tract of the patient, said cylindrical body having a radially outwardly extending concentric flange for location at the interior side of the wall of the gastrointestinal tract to inhibit movement of the cylindrical body out of the patient;
- means, attached around the circumferential surface of the cylindrical body, for facilitating fixation of the tissue of the abdominal wall to the cylindrical body including a cylindrical sleeve of dacron foam glued to the cylindrical body;
- a flange member, threaded concentrically on the cylindrical body for tightening against the external surface of the abdominal wall to inhibit movement of the cylindrical body into the patient and to permit adjustment of the apparatus for variations in thickness of the abdominal wall;
- a valve mechanism including
  - a valve body;
  - a spring means for biasing the valve body; and
  - a threaded sleeve concentric with the cylindrical body for selectively securing the valve mechanism in position and alternatively, selectively releasing the valve mechanism to permit the removal of the valve mechanism from the cylindrical body;
- wherein the valve body is moveable along the axis of the cylindrical body responsive to the insertion into the apparatus of the coupling of a extracorporeal conduit, and wherein removal of the threaded sleeve permits removal of the valve mechanism for cleaning.

* * * * *

UNITED STATES PATENT AND TRADEMARK OFFICE
CERTIFICATE OF CORRECTION

PATENT NO. : 4,344,435
DATED : August 17, 1982
INVENTOR(S) : Norbert T. Aubin

It is certified that error appears in the above—identified patent and that said Letters Patent is hereby corrected as shown below:

On Title Page, Item 76 should read as follows:

[76] Inventor: Norbert T. Aubin (deceased), P.O. Box 982, Loma Linda, Calif. 92324 (sole heir: Ann Rasmussen, P.O. Box 1226, Yucca Valley, Calif. 92284)

Signed and Sealed this

Sixteenth Day of November 1982

[SEAL]

Attest:

GERALD J. MOSSINGHOFF

Attesting Officer — Commissioner of Patents and Trademarks